United States Patent
Bagwell et al.

(10) Patent No.: US 9,131,988 B2
(45) Date of Patent: Sep. 15, 2015

(54) SELF POSITIONING TRACHEAL TUBE CLEARANCE MECHANISM USING SKIVES

(71) Applicant: AVENT, INC., Alpharetta, GA (US)

(72) Inventors: Alison S. Bagwell, Alpharetta, GA (US); Stephen A. Baratian, Roswell, GA (US); Jennifer S. Stadelman, Alpharetta, GA (US); Scott M. Teixeira, Cumming, GA (US); Joseph A. Cesa, Cumming, GA (US); Benone Tarcau, Buford, GA (US); John Brewer, Marietta, GA (US)

(73) Assignee: AVENT, INC., Alpharetta, GA (US)

( * ) Notice: Subject to any disclaimer, the term of this patent is extended or adjusted under 35 U.S.C. 154(b) by 11 days.

(21) Appl. No.: 14/026,157

(22) Filed: Sep. 13, 2013

(65) Prior Publication Data

US 2014/0090642 A1    Apr. 3, 2014

Related U.S. Application Data

(60) Provisional application No. 61/707,259, filed on Sep. 28, 2012.

(51) Int. Cl.
| | | |
|---|---|---|
| *A61M 16/04* | (2006.01) | |
| *A61B 19/00* | (2006.01) | |
| *A61M 25/00* | (2006.01) | |

(52) U.S. Cl.
CPC .............. *A61B 19/34* (2013.01); *A61M 16/04* (2013.01); *A61M 16/0434* (2013.01); *A61M 16/0463* (2013.01); *A61M 2025/0019* (2013.01); *A61M 2209/10* (2013.01)

(58) Field of Classification Search
USPC .................. 15/300.1, 104.1, 104.05, 104.03, 15/104.33, 104.16, 104.2, 164, 206
See application file for complete search history.

(56) References Cited

U.S. PATENT DOCUMENTS

| 5,003,657 A | | 4/1991 | Boiteau et al. | |
|---|---|---|---|---|
| 5,168,593 A | * | 12/1992 | Poje et al. | ..................... 15/104.2 |
| 5,297,310 A | * | 3/1994 | Cox et al. | ......................... 15/106 |
| 5,535,756 A | * | 7/1996 | Parasher | ....................... 600/569 |
| 5,702,413 A | * | 12/1997 | Lafontaine | ..................... 606/159 |
| 5,836,032 A | * | 11/1998 | Hondo | ........................ 15/104.32 |
| 6,775,873 B2 | * | 8/2004 | Luoma | ........................ 15/104.33 |

(Continued)

FOREIGN PATENT DOCUMENTS

| DE | 2010 026 774 A1 | 1/2012 |
|---|---|---|
| GB | 2 482 618 A | 2/2012 |

(Continued)

OTHER PUBLICATIONS

Co-pending U.S. Appl. No. 14/026,122, filed Sep. 13, 2013, by Stadelman et al. for "Self Positioning Tracheal Tube Clearance Mechanism Using a Collar.".

(Continued)

*Primary Examiner* — Dung Van Nguyen
(74) *Attorney, Agent, or Firm* — Dority & Manning, PA

(57) ABSTRACT

A device for cleaning the interior wall of a catheter has a cleaning lumen and skives as non-inflatable removal elements on the exterior surface of the cleaning lumen. Each skive has a first position when unconstrained and a second position when within the catheter. The skives self-position the device concentrically within the catheter. Suction is desirably applied to the cleaning lumen during use.

18 Claims, 1 Drawing Sheet

(56) References Cited

U.S. PATENT DOCUMENTS

| | | |
|---|---|---|
| 8,157,919 B2 | 4/2012 | Vazales et al. |
| 2003/0209258 A1 | 11/2003 | Morejon |
| 2004/0092956 A1 | 5/2004 | Liddicoat et al. |
| 2007/0038226 A1 | 2/2007 | Galdonik et al. |
| 2007/0293812 A1 | 12/2007 | Wright et al. |
| 2010/0264046 A1* | 10/2010 | Bates et al. .................. 206/223 |
| 2010/0331853 A1* | 12/2010 | Garcia et al. .................. 606/110 |
| 2011/0023885 A1 | 2/2011 | Vazales et al. |
| 2011/0186052 A1 | 8/2011 | Morejon |

FOREIGN PATENT DOCUMENTS

| | | |
|---|---|---|
| WO | WO 94/03226 A1 | 2/1994 |
| WO | WO 2011/126812 A1 | 10/2011 |

OTHER PUBLICATIONS

Co-pending U.S. Appl. No. 14/026,139, filed Sep. 13, 2013, by Stadelman et al. for "Self Positioning Tracheal Tube Clearance Mechanism Using Whisks.".

* cited by examiner

SELF POSITIONING TRACHEAL TUBE CLEARANCE MECHANISM USING SKIVES

The present disclosure relates to cleaning mechanisms for the central (breathing) lumen of tracheal tubes.

Tracheal intubation involves the insertion of a hollow tubular device, known as a tracheal tube, into the trachea of a patient. The tube may be inserted through the mouth or, less desirably, the nose or may be inserted through the neck by way of an incision in the front of the throat. If inserted through the mouth or nose the tube is referred to as an endotracheal tube, if through the front of the throat the tube is referred to as a tracheostomy or trach tube. The two types of tubes will be referred to as tracheal tubes herein. The tracheal tube passes into the trachea and terminates at a position above the carina, anterior to a position between the second and fourth thoracic vertebrate. Gases may then be introduced through the central lumen of the tracheal tube and into the lungs of the patient.

The primary purpose of tracheal intubation is to mechanically ventilate the patient's lungs when the patient is incapable of normal breathing induced ventilation. Intubation may also be used to apply anesthetic gases during surgical intervention. It is desirable to seal the passageway around the tracheal tube in order to maintain enough air pressure to force the air into the lungs during mechanical ventilation and to prevent escape of gases past the tube (i.e. "short circuiting" or bypassing of the lungs). Such a seal may be produced by the use of an inflatable cuff or balloon surrounding the tracheal tube near its distal end. When the tracheal tube has been introduced into the patient's trachea, the inflatable cuff will normally be located about 3 to 5 centimeters above the carina and within the tube-like trachea.

Once inflated, the cuff will engage the wall of the trachea and thereby seal the trachea and prevent the gases being introduced through the tracheal tube from simply reversing course after exiting the distal end of the tube and traveling back up and around the tube to exit the mouth. While treatment of this sort has proved successful for patients having chronic or acute respiratory diseases, there is a constant risk of several complications.

One of the most common complications in mechanical ventilation is known as ventilator associated (or acquired) pneumonia or VAP. Patients receiving tracheal intubation sometimes develop this pneumonia from an infection of the lungs, possibly induced by contaminated secretions, mucus or biofilm entering the trachea and the lungs after growing in the warm, moist environment in the central lumen of the tracheal tube. Removing these secretions from the tracheal tube lumen would likely reduce the risk of such infections.

In addition, it has been reported that extubated endotracheal tubes had significantly decreased luminal volume and radius compared to unused tubes. Even small changes in the luminal radius result in large changes in resistance to airflow-leading to an increased work of breathing, difficulty in breathing and increased length of hospital stays. The build-up of tenacious secretions within the tracheal tube can lead to difficulty in weaning off the mechanical ventilator, the need for emergency tracheal tube replacement, or the need for tracheostomy, all of which place the patient at greater risk of additional complications.

A number of attempts have been made to develop cleaning mechanisms for the central lumen of tracheal tubes. UK patent application GB 2482618 to Airway Medix Spolka Z.O.O. discusses a cleaning device having a balloon on the distal end and having a source of pressurized liquid and a source of suction to wash the interior of the central lumen and remove the liquid and biofilm. U.S. Pat. No. 8,157,919 to Endoclear LLC provides a medical tube cleaning apparatus with a mechanically actuated, non-inflatable cleaning member. No liquid or suction are used.

What is needed is a mechanism for thorough cleaning of the central tracheal tube lumen.

SUMMARY

This disclosure relates to a device (cleaning device, self-positioning cleaning device, or self-positioning tracheal tube cleaning device) for cleaning the interior walls of the breathing lumen, e.g., a catheter or tracheal tube. The device has a cleaning lumen and non-inflatable removal elements and these elements have a first position and a second position with respect to the cleaning lumen. The removal elements are skives. Each skive has a tip, intermediate region, and an end junction. Each skive is joined to the cleaning lumen via the end junction.

The skives are on the exterior surface of the cleaning lumen and change from a first position, where the tips have a maximum distance from the cleaning lumen when the skives are unconstrained, to a second position, where the tips are less than the maximum distance from the cleaning lumen, e.g., when the device is within the catheter. The skives center the cleaning lumen with respect to the interior wall of the breathing lumen when the radially protruding distance of the skives from the cleaning lumen plus the outer diameter of the cleaning lumen are greater than the interior diameter of the breathing lumen. In this way the breathing lumen interior contacts the tips of the skives. Suction is desirably applied to the cleaning lumen during use.

DETAILED DESCRIPTION

Figure 3:
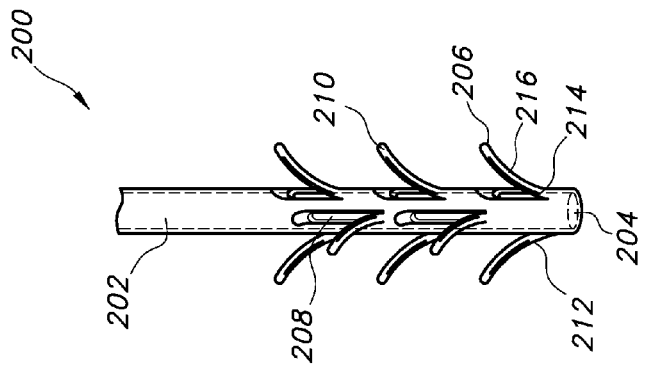
FIG. 3 shows a cleaning device having skives outside of the cleaning lumen. The cleaning lumen, port and skives and skive openings are clearly visible.

Reference will now be made in detail to one or more embodiments, examples of which are illustrated in the drawings. It should be understood that features illustrated or described as part of one embodiment may be used with another embodiment to yield still a further embodiment.

Suction catheters are well known and widely commercially available for many medical uses. Suctioning may be performed using an "open" or "closed" system. In the open system, the suction catheter is a flexible plastic tube that is inserted into the tracheal tube breathing lumen with a source of suction connected to the proximal end of the suction catheter. Anything that the suction catheter touches before entering the lumen is preferably maintained in a sterile condition so a "sterile field" is created on or next to the patient. The suction catheter must be carefully handled after it is used since it will be coated with the patient's secretions. In contrast, in the "closed" system, for example that disclosed in U.S. Pat. No. 4,569,344, a device which may be used to suction secretions is enclosed within a generally cylindrical plastic bag to eliminate or minimize contamination of the suction catheter prior to use. This is generally referred to as a "closed suction catheter" and is available under the trade name TRACH CARE® (BALLARD® Medical Products) from Kimberly-Clark Corporation.

Disclosed is a device that enters the tracheal tube either by opening the ventilation circuit or by entering through an access port that gives access to the tracheal tube. The device has a proximal end, a distal end, and skives between these ends. The distal end of the device enters the tracheal tube first. The device may contain markings which indicate its advancement through the tracheal tube and may convey to the user information about the location of the device within the tracheal tube, e.g., when the distal end of the device reaches the distal end of the tracheal tube. The cleaning lumen of the device must of course be slightly smaller than the interior diameter of the tracheal tube. The skives must deform to fit within the interior of the tracheal tube and the tips point towards the proximal end of the device when the skives are in the first or second positions. The skives take on a second position when the device is inserted within the interior of the tracheal tube.

The skives strive to take on the first position, the unconstrained position, due to an intentional bias for each skive tip to be a predetermined maximum distance away from the exterior of the cleaning lumen.

Suction is desirably applied to the cleaning lumen during use.

The removal elements self-position the device to be concentric with the tracheal tube when the cleaning lumen is in the tracheal tube. This self-positioning is caused by the bias of the removal elements, their spacing around the cleaning lumen, and the radial dimensions of the cleaning lumen and the tracheal tube interior.

Figure 1:
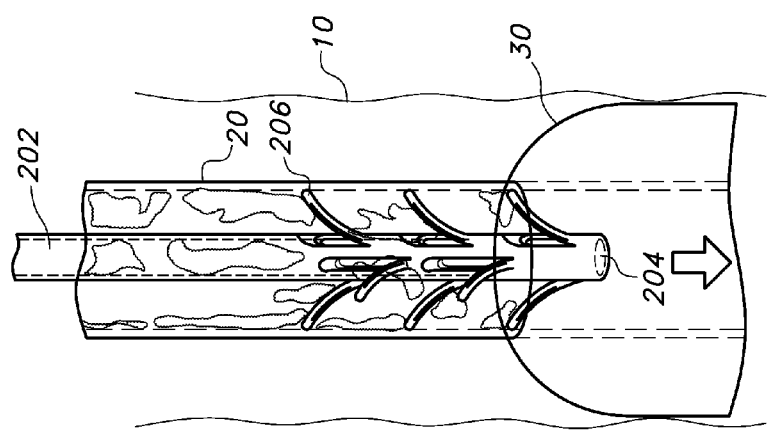
FIG. 1 is a drawing showing a self-positioning tracheal tube cleaning device having skives entering a tracheal tube, as indicated by the arrow.

In the conventional use of an endotracheal tube, air is delivered to the patient's lungs through the breathing lumen or tracheal tube 20. The tube 20 has a balloon cuff 30 that desirably seals against the trachea 10 such that secretions above the cuff and outside the tube do not move downwardly into the lungs (FIG. 1). Further discussion of the functioning to the balloon cuff may be found, for example, in U.S. Pat. No. 6,802,317 to Goebel. Mucus may nevertheless build up within the breathing channel or lumen of the tube, causing a decrease in the cross-sectional area of the lumen, thus increasing the resistance to air flow within the lumen and so decreasing the air flow to the patient's lungs. The mucus may also harbor unwanted bacteria that may thrive in the warm, moist environment inside the tube.

FIG. 1 shows a self-positioning cleaning device 200 entering a catheter, e.g. a tracheal tube 20, as indicated by the arrow. The cleaning device 200 may be a modified closed suction catheter as described above. This device 200 has an optional port 204 on the distal end of the cleaning lumen 202 and has removal elements that are skives (or petals, tines or flaps) 206 along the exterior surface of the cleaning lumen 202. It is believed that a minimum of three skives 206 are needed to self-center the cleaning device and that they should be equally spaced about the cleaning lumen, e.g. 120 degrees from each other when there are only three skives. Each skive 206 has a tip 210 that is separated from the cleaning lumen 202. Generally opposite the tip 210 of each skive 206 is a bend region 212 with a junction end 214 that attaches to the cleaning lumen 202. Each skive 206 has an intermediate portion 216 between the tip 210 and the bend region 212. The distance between the end of the tip 210 and the junction end 214 is longer than the radial distance between the exterior surface of the cleaning lumen 202 and the interior of the trach tube 20 when the cleaning lumen 202 is concentric within the trach tube 20. The skives may be of different lengths but are desirably about the same length.

The skives 206 reversibly bend or deflect outward (away from the exterior of the cleaning lumen 202) and this bending at least occurs in the bend region 212 and/or the junction end 214. The tip 210 and intermediate portions 216 of the skives 206 can also reversibly bend outwardly with respect to the exterior of the cleaning lumen 202. The skives 206 can also have cross-sectional shapes between the tip 210 and the bend region 212 that are generally bowed or curved, with the concave portions facing towards the exterior of the cleaning lumen 202. The tips 210 are biased to extend outward from the exterior surface of the cleaning lumen. The skives 206 may have shapes as shown in the Figures or may have a tip 210 that is larger or smaller than the bend region 212 and taper therebetween.

The removal element skives 206 wipe the interior of the tracheal tube which results in the removal of secretion buildup every time the cleaning device is retracted within the tracheal tube (moved away from distal end of the tracheal tube). The tips and intermediate portions of the skives 206 deflect inwardly towards the cleaning lumen 202 by contact of at least the tips with the interior wall of the tracheal tube 20 as the cleaning lumen 202 is inserted into the tracheal tube 20. In the absence of constraining forces that push them inwards, at least the tips 210 are biased to extend away from the exterior surface of the cleaning lumen 202. In the absence of any constraining forces this bias has the tips 210 of the skives 206 point in the direction of the proximal end of the device. This bias also causes the tips 210 to contact the interior wall of the tracheal tube and/or accumulated mucus, secretions, etc. inside a tracheal tube 20 when the tracheal tube has an inner radius that is smaller than the radial distance of the end of the tip of the skive from the exterior surface of the cleaning lumen; the skives 206 bend outward at least in their bend regions 212 to deploy the skives 206 outwardly against the tracheal tube 20 wall. The outward deployment of the skives 206 puts increased pressure on the tracheal tube 20 wall to remove mucus.

The skives 206 can be created by cutting into (skiving) the cleaning lumen 202 at an angle. In this way the skives 206 may be formed from a part of the cleaning lumen 202 as a unitary structure and are desirably not a separate piece that has been attached to the lumen 202. Skives 206 may also formed as separate pieces that are attached to the cleaning lumen. Separate pieces raise some concern that they may break off more easily than a unitary structure and may be aspirated by a patient. Skive openings 208 can be included in the device 200 near or adjacent the skives 206 at the junction end 214. The skive openings 208 can be in fluid communication with the interior of the cleaning lumen 202.

Figure 2:
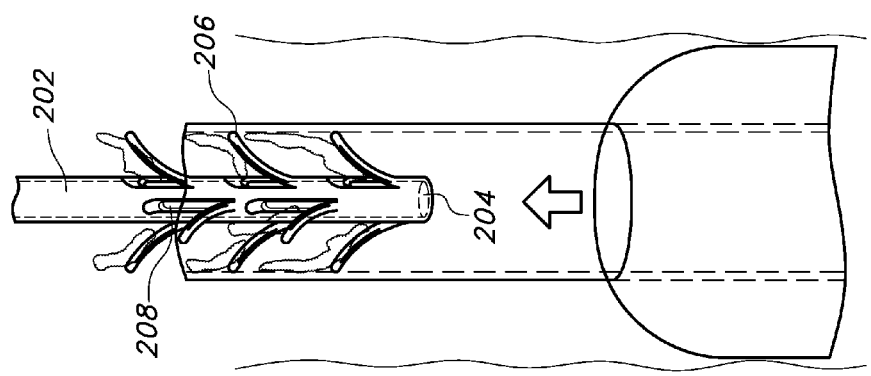
FIG. 2 shows a cleaning device having skives being withdrawn from the tracheal tube, as indicated by the arrow.

FIG. 2 shows the cleaning device 200 being withdrawn from the tracheal tube 20, as indicated by the arrow. The skives 206 contact the inner walls of the tube 20 as the device 200 is withdrawn, loosening any deposits and directing them toward the skive openings 208 or toward the junction end 214. Suction applied to the proximal end (not shown) of the device 200 helps pull the deposits into the cleaning lumen 202 through the skive openings 208 if present, i.e., if they are in fluid communication with the suction, and the distal port 204.

FIG. 3 shows the cleaning device 200 outside of the tracheal tube. The cleaning lumen 202, port 204 and skives 206 and skive openings 208 are clearly visible.

While the present disclosure has been described in connection with certain preferred embodiments it is to be understood that the subject matter encompassed by way of the present disclosure is not to be limited to those specific embodiments. On the contrary, it is intended for the subject matter of the disclosure to include all alternatives, modifications and equivalents as can be included within the spirit and scope of the following claims.

We claim:

1. A device for cleaning an interior wall of a catheter, the device comprising: a cleaning lumen having an exterior surface with skives, said skives capable of changing from a first position to a second position, wherein the skives take on the second position when the device is inserted within the catheter;
   wherein the skives have a tip and a junction end and a distance between the tip and the junction end is longer than the radial distance between the exterior surface of the cleaning lumen and the interior wall of the catheter when the cleaning device is centered within the catheter; and
   wherein the skives bend away from the cleaning lumen at least in their bend regions to deploy the skives against the interior wall of the catheter.

2. The device of claim 1, wherein said catheter is a tracheal tube, and wherein said skives in said second position center the device within the tracheal tube with respect to the interior wall.

3. The device of 1, wherein the tips and intermediate portions of the skives can reversibly bend with respect to the exterior surface of the cleaning lumen.

4. The device of claim 1, wherein the skives have cross-sectional shapes between the tip and the bend region that are generally bowed or curved to make a concave portion facing towards the exterior surface of the cleaning lumen.

5. The device of claim 1, wherein suction is applied to a proximal end of said cleaning lumen to pull the deposits into the cleaning lumen through the skive openings if present, and through a distal port.

6. A device for cleaning deposits from an interior wall of a catheter, the device comprising:
   a cleaning lumen having an exterior surface and a distal end;
   a port at the distal end, the port in fluid communication with the cleaning lumen; and
   a plurality of removal elements along the exterior surface of the cleaning lumen,
   wherein suction applied to a proximal end of the device pulls the deposits into the cleaning lumen through the port.

7. The device of claim 6, wherein each removal element comprises a tip and a bend region, and wherein each removal element has a cross-sectional shape between the tip and the bend region that is generally bowed or curved such that a concave portion of the cross-sectional shape faces toward the exterior surface of the cleaning lumen.

8. The device of claim 6, wherein each removal element comprises a tip and a bend region, and wherein the tip is larger than the bend region such that the removal element tapers between the tip and the bend region.

9. The device of claim 6, wherein each removal element comprises a tip and a bend region, and wherein the tip is smaller than the bend region such that the removal element tapers between the tip and the bend region.

10. The device of claim 6, further comprising an opening positioned adjacent a junction end of each removal element and in fluid communication with the cleaning lumen, and wherein suction applied to a proximal end of the device pulls the deposits into the cleaning lumen through the openings.

11. The device of claim 6, wherein the removal elements are formed from a part of the cleaning lumen as a unitary structure.

12. A device for cleaning an interior wall of a catheter, the device comprising:
   a cleaning lumen having an exterior surface with skives, each skive having a tip, an intermediate portion, and a bend region,
   wherein each skive has a cross-sectional shape between the tip and the bend region that is generally bowed or curved such that a concave portion of the cross-sectional shape faces toward the exterior surface of the cleaning lumen.

13. The device of claim 12, wherein the bend region is generally opposite the tip of each skive and the intermediate portion is between the tip and the bend region.

14. The device of claim 12, wherein the cathether is a tracheal tube, and wherein the tips and intermediate portions of the skives deflect inwardly toward the cleaning lumen by contact of at least the tips with the interior wall of the tracheal tube.

15. The device of claim 12, wherein the catheter has an interior, and wherein the skives deform to fit within the interior of the catheter.

16. The device of claim 12, wherein the skives self-position the device to be concentric with the catheter when the cleaning lumen is in the catheter.

17. The device of claim 12, wherein the skives are equally spaced about the cleaning lumen.

18. The device of claim 12, further comprising a port at a distal end of the cleaning lumen, the port in fluid communication with the cleaning lumen.

* * * * *